(12) United States Patent
Rodriguez

(10) Patent No.: US 7,407,055 B2
(45) Date of Patent: Aug. 5, 2008

(54) HAIR ROOTS COLORING KIT

(76) Inventor: Deborah T. Rodriguez, 66 Forbes St., Riverside, IL (US) 60546

(*) Notice: Subject to any disclaimer, the term of this patent is extended or adjusted under 35 U.S.C. 154(b) by 481 days.

(21) Appl. No.: 10/672,338

(22) Filed: Sep. 25, 2003

(65) Prior Publication Data
US 2005/0067320 A1 Mar. 31, 2005

(51) Int. Cl.
*A45D 19/00* (2006.01)
(52) U.S. Cl. ............... 206/581; 132/208; 8/400; 8/405; 206/571
(58) Field of Classification Search ........... 206/223, 206/229, 823, 581, 570, 571, 568; 132/208; 8/405–410
See application file for complete search history.

(56) References Cited

U.S. PATENT DOCUMENTS

| 1,056,218 | A | * | 3/1913 | Sahl | 383/40 |
| 1,081,788 | A | * | 12/1913 | Terry | 206/581 |
| 2,789,689 | A | * | 4/1957 | Lewis | 206/459.5 |
| 4,294,293 | A | * | 10/1981 | Lorenz et al. | 141/100 |
| 4,506,783 | A | * | 3/1985 | Morganroth | 206/581 |
| 4,823,985 | A | * | 4/1989 | Grollier et al. | 222/1 |
| 5,209,565 | A | * | 5/1993 | Goncalves | 366/130 |
| 5,551,454 | A | * | 9/1996 | Goncalves | 132/208 |
| 5,554,197 | A | * | 9/1996 | Assini et al. | 8/406 |
| 5,884,771 | A | * | 3/1999 | McCormick | 206/581 |
| 6,440,175 | B1 | * | 8/2002 | Stanley, III | 8/405 |
| 6,835,018 | B2 | * | 12/2004 | Miczewski et al. | 401/196 |

* cited by examiner

*Primary Examiner*—Mickey Yu
*Assistant Examiner*—Jerrold Johnson

(57) ABSTRACT

A hair roots coloring kit includes a plurality of kit components carried in a drawstring bag for mixing and applying standard hair coloring materials to the uncolored outgrown roots of a user's hair. One or more measuring devices such as a measuring cup, a syringe, or an eyedropper are used for measuring the hair coloring materials to produce a matching color to previously colored hair shafts of the hair. A reusable mixing bowl or a plurality of disposable mixing bowls hold the measured hair coloring materials. A reusable stirring stick or a plurality of disposable stirring sticks are provided for mixing together the measured hair coloring materials in the mixing bowl. An applicator brush is used for applying the mixed matching color of hair coloring composition to the uncolored hair roots. A pair of protective gloves are provided to protect the user's hands during application of the hair coloring composition to the hair roots. A cleaning brush is used to aid in cleaning the kit components following use.

25 Claims, 2 Drawing Sheets

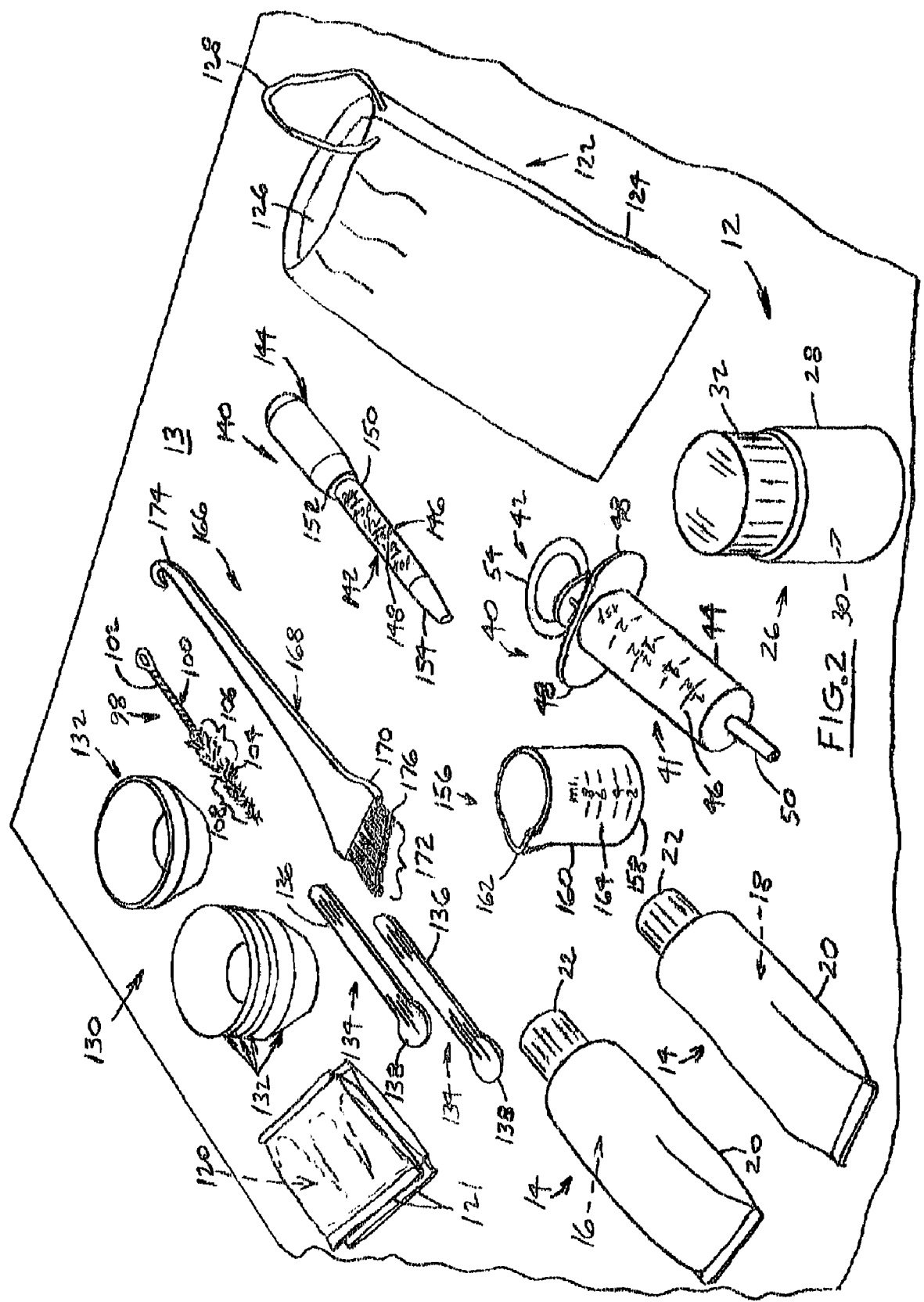

HAIR ROOTS COLORING KIT

BACKGROUND OF THE INVENTION

1. Field

Figure 1:
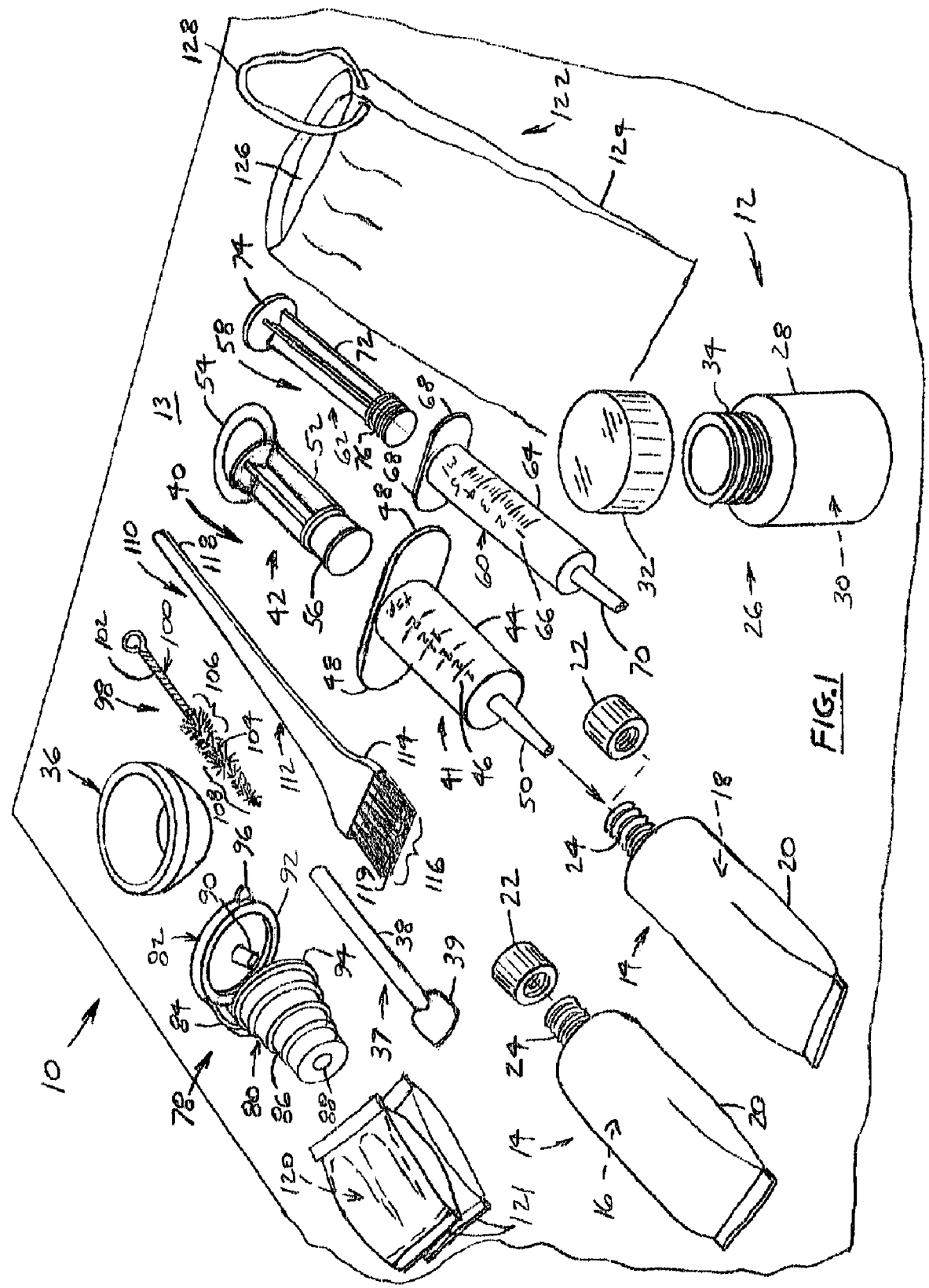

The present invention relates generally to hair coloring tools and methods for mixing hair coloring compositions, and more particularly to a portable hair coloring kit and method for mixing hair coloring compositions to color roots of the user's hair to a matching color to the hair shafts.

2. State of the Art

Hair coloring has been done for hundreds if not thousands of years by women to change and enhance their appearance and to cover graying hair. More recently, men have increasingly colored their hair generally for the same reasons. In the past hair coloring dyes were based on naturally occurring dyes such as those produced by plants or various minerals. In modern times, there are numerous hair coloring products, including coloring shampoos and weekly rinses, semi-permanent hair coloring compositions, and permanent hair coloring compositions.

Many hair coloring products require mixing together of two or more components prior to application to the user's hair, such as a liquid or paste hair coloring composition and a liquid developer or fixing solution. The liquid hair coloring composition may be packaged in a squeeze bottle and the hair coloring paste may be packaged in a squeeze tube. The hair dresser typically mixes the required quantities of hair coloring composition and fixing solution in a bowl or similar container. The mixed coloring composition is applied to the user's hair using one of a number of types of brushes commercially available for the task similar in design to paint brushes.

Coloring may be done of all the user's hair or only to portions of the hair such as in "streaking" the hair. Touch-up coloring is required following full coloring to color the hair roots grown out since the last hair coloring to match the color of the previously colored hair shafts. This may require blending or mixing together of hair coloring compositions of several different colors to match the previously colored hair shafts. Usually a minimum amount of the hair coloring composition is prepared to do the job as the hair coloring materials are quite expensive.

In an effort to more conveniently mix hair coloring compositions of different colors, a hair coloring kit which better enables a user to mix custom colors of hair coloring compositions is disclosed in U.S. Pat. No. 6,440,175 issued to Stanley, III. The kit includes a liquid base composition, a plurality of color concentrates, and a dispenser. The color concentrates provided include the colors green, yellow, blue, red, orange, brown, white, black or any other colors such as purple or any other shades or variations of these colors. The color concentrates can be provided as liquids packaged in respective containers such as vials with a medicine dropper, syringe or eye dropper for transferring the color concentrate from the vials for mixing with the base composition. Alternatively, the vials may each be provided with a cap such that the color concentrates are poured from the respective vials. The color concentrates are mixed with the base composition in the dispenser to form a custom color. The hair coloring composition of the custom color is then sprayed onto the user's hair. The base composition can be a conventional hair spray which also holds the user's hair in place. The base composition could also be a tablet or powder that is mixed with water to form the liquid base composition.

The kit of Stanley, III has several substantial shortcomings. Firstly, the kit cannot be used to mix conventional hair coloring materials which may be quite close to the desired color, requiring only slight tinting. Rather, the basic green, yellow, blue, red, orange, brown, white, black must be mixed to produce the desired color. This can be very difficult to produce the desired color. Likewise, the kit cannot interface with the containers used to package conventional hair coloring materials. Finally, the kit does not provide a sufficient measuring devices for portioning the color concentrates and base composition, provides no mixing device such as a stirring stick, provides no application brush or similar application device, provides no protective gloves, provides no cleaning brush or similar device, and provides no carrying device such as a carrying bag or carrying case.

Therefore, there is a need for a hair coloring kit for use with conventional hair coloring materials which provides a complete set of kit components to conduct the hair coloring process. This might include a container device, one or more measuring devices, a stirring device, protective gloves, an applicator device, and a container in which to store the kit components during periods of non-use. The kit would include cleanable, reusable kit components and/or a plurality of disposable kit components.

SUMMARY OF THE INVENTION

The present invention is a hair roots coloring kit and a method for coloring the roots of a user's hair. The kit and method are for mixing together standard hair coloring materials including containers of a plurality of different colored hair coloring compositions and various fixing agents. The hair coloring compositions are mixed to form a matching color of hair coloring composition to a user's previously colored hair shafts for applying to uncolored outgrown roots of the hair since the last coloring. Hair coloring materials packaged in any of the standard containers may be used including squeezable tubes containing the hair coloring composition in the form of a hair coloring paste and fixing agents in variously sized bottles.

The hair roots coloring kit includes at least one measuring device adapted for measuring necessary quantities of the hair coloring materials to produce the matching color of hair coloring composition. A mixing container is adapted for holding the necessary quantities of the hair coloring materials. A stirring device is adapted for manual mixing together of the necessary quantities of the hair coloring materials within the container to produce the matching color of hair coloring composition. An applicator device is adapted for manually applying the matching color of hair coloring composition to the roots of the user's hair. A carrying device is adapted for receiving the measuring device, the stirring device, and the applicator device for storage and transport thereof.

A preferred hair roots coloring kit includes the at least one measuring device comprising a measuring cup, a syringe, or an eyedropper. The mixing container comprises a single reusable mixing bowl or a plurality of disposable mixing bowls. The stirring device comprises a single reusable stirring stick or a plurality of disposable stirring sticks. The applicator comprises an applicator brush having an elongate handle from which a plurality of bristles extend. The carrying device comprises a drawstring bag. The further comprises an additional kit component of a pair of protective gloves and/or and a cleaning brush. The kit further includes a bottle stopper which includes an attached recloseable cap, the body being adapted to closely fit within the necks of variously sized bottles and having a longitudinal bore which extends through the body.

The method for coloring the roots of a user's hair includes the steps of: 1) providing a plurality of containers of hair coloring materials including different colored hair coloring compositions; 2) providing a carrying device and a plurality of coloring kit components including at least one measuring device, a mixing container, a stirring device, and an applicator device contained therein; 3) removing the coloring kit components from the carrying device; 4) opening the containers of hair coloring materials; 5) measuring necessary quantities of the hair coloring materials removed from the containers using measuring device to form a matching color of hair coloring composition to the user's hair and depositing into the mixing container; 6) manually mixing together the necessary quantities of the hair coloring materials within the mixing container using the stirring device to form the matching color of hair coloring composition; 7) manually applying the matching color of hair coloring composition from the mixing container onto the roots of the user's hair using the applicator device; 8) preparing the coloring kit components for storage; and 9) replacing the coloring kit components into the carrying device.

In a preferred method the step of providing a plurality of containers of hair coloring materials includes providing a hair coloring composition in the form of a hair coloring paste packaged in a squeezable tube having an outlet neck. The step of providing a carrying device and a plurality of coloring kit components includes providing a measuring device comprising a syringe having an elongate tapered needle adapted to be closely received within the neck of the squeezable tube. The step of measuring necessary quantities of the hair coloring materials includes inserting the tapered needle within the neck and squeezing the tube to receive the hair coloring paste therefrom. The plurality of coloring kit components provided are of a cleanable reusable type. The step of preparing the coloring kit components for storage comprises cleaning the coloring kit components. The step of providing a carrying device and a plurality of coloring kit components includes providing a plurality of disposable mixing containers and stirring devices. The step of preparing the coloring kit components for storage comprises disposing of used mixing containers and stirring sticks, and cleaning the other coloring kit components used. The step of providing a carrying device and a plurality of coloring kit components includes providing a pair of protective gloves and a cleaning brush. At least some of the plurality of coloring kit components provided are of a cleanable reusable type. The step of preparing the coloring kit components for storage comprises cleaning at least some of the coloring kit components using the which are of the cleanable reusable type using the cleaning brush. Further comprising the steps of putting on the protective gloves prior to measuring necessary quantities of the hair coloring materials and removing the protective gloves after applying the matching color of hair coloring composition to the roots of the user's hair.

THE DRAWINGS

The best mode presently contemplated for carrying out the invention is illustrated in the accompanying drawings, in which:

FIG. 1 is a perspective view of a first embodiment hair roots coloring kit of the present invention as used with hair coloring materials; and FIG. 2, a perspective view of a second embodiment hair roots coloring kit of the present invention as used with the hair coloring materials.

DETAILED DESCRIPTION OF THE ILLUSTRATED EMBODIMENTS

Shown in FIG. 1 is a first embodiment hair roots coloring kit of the present invention, designated generally at 10, shown with conventional hair coloring materials 12 disposed on a table surface 13. The hair roots coloring kit 10 is used for mixing together any of a variety of types standard commercially available hair coloring materials, including dyes and other hair coloring compositions, fixing agents, and others which come in containers such as squeeze tubes, squeeze bottles, non-squeezable bottles, and the like.

Typical hair coloring materials 12 include a plurality of squeeze tube assemblies 14 containing a plurality of different colored hair coloring compositions in the form of hair coloring compositions 16 and 18 in the form of paste. The hair coloring compositions 16 and 18 are for mixing together to form a matching color of hair coloring composition to a user's previously colored hair shafts to apply to uncolored outgrown roots of the hair. The squeeze tube assemblies 14 each include a flexible tube 20 and a screw cap 22 which threads onto a threaded outlet neck 24 of the tubes 20 to seal the respective hair coloring compositions 16 and 18 in the tubes 20 until needed. A bottle assembly 26 includes a semi-rigid bottle 28 which contains a fixing solution 30 used to set the matching color of hair coloring composition prior to application to the hair roots. The bottle assembly 26 includes a screw cap 32 which threads onto a threaded neck 34 of the bottle 28 to seal the fixing solution 30 therein until needed.

The coloring kit 10 includes a plurality of kit components such as a mixing container for holding the necessary quantities of the hair coloring materials to produce the matching color of hair coloring composition. A mixing container comprises a first mixing bowl 36 made of a substantially rigid and cleanable material such as glass, ceramic, or plastic so as to be reusable. The mixing bowl 36 is used to contain the different colors of hair coloring compositions 16 and 18 during mixing together to form the matching color for the hair and for mixing in the fixing solution 30 to set the matching color prior to applying to the hair roots.

Another kit component is a stirring device comprising a first stirring stick 37 for manually mixing together of the necessary quantities of the hair coloring materials 16 and 18 within the mixing bowl 36 to produce the matching color of hair coloring composition. The stirring stick 37 is reusable, being made of a substantially rigid and cleanable material such as plastic, glass, or wood. The stirring stick 37 includes an elongate handle 38 of a round cross-section and a dependent flat spatula 39 for mixing of the hair coloring compositions 16 and 18, and the fixing solution 30 in the mixing bowl 36.

Another kit component is at least one measuring device provided for measuring the necessary quantities of the hair coloring compositions 16 and 18 to produce the matching color of hair coloring composition. A first measuring device comprises a large syringe 40 for measuring the necessary quantities of hair coloring compositions 16 and 18 squeezed from the tubes 20. The large syringe 40 includes a hollow body 41 which closely receives a slidable plunger 42. The body 41 is made of plastic having a transparent tubular mid-section 44 with a measuring indicia 46, a pair of finger engaging tabs 48, and a tapered needle 50 sized to be closely received within the necks 24 of tubes 20. The plunger 42 includes a longitudinally ribbed mid-section 52 and an integral thumb ring 54 made of plastic, and a resilient sealing piston 56 made of a rubber-like material affixed opposite thumb ring 54. The piston 56 and mid-section 52 of plunger 42 closely fit within the mid-section 44 of body 41. The large syringe 40 receives the hair coloring compositions 16 and 18 contained therein upon squeezing of the tubes 20 causing plunger 42 to partially withdraw from body 41. The thumb ring 54 is provided to facilitate withdrawal of the plunger 42 from the body 41 as the hair coloring composition 16 and 18 is squeezed from the tubes 20 into the large syringe 40.

Another kit component is a second measuring device comprising a small syringe 58 for measuring the fixing solution 30 from the bottle 28. The small syringe 58 includes a hollow body 60 which closely receives a slidable plunger 62. The body 60 is made of plastic having a transparent tubular mid-section 64 with a measuring indicia 66, a pair of finger engaging tabs 68, and a tapered needle 70. The plunger 62 includes a longitudinally ribbed mid-section 72 and an integral finger disk 74 made of plastic, and a resilient sealing piston 76 made of a rubber-like material affixed opposite finger disk 74. The piston 76 and mid-section 72 of plunger 62 closely fit within the mid-section 64 of body 60. The needle 70 receives the fixing solution 30 contained in bottle 28 as explained subsequently.

Another kit component is a bottle stopping device comprising a recloseable bottle stopper 78 which includes a longitudinally tapered, resilient body 80 of circular cross-section made of a rubber-like material, and an integral recloseable cap 82 of a disk-shape attached to the body 80 by a connecting strap 84. An outer surface 86 of the body 80 is annularly stepped for closely fitting within the necks 34 of variously sized bottles 28 containing the fixing solution 30 after the screw cap 32 is removed. A longitudinal bore 88 extends through the body 80 to allow the fixing solution 30 to flow therethrough. An externally opening portion (not shown) of the bore 88 is of such a size to closely receive the needle 70 of the small syringe 58. The cap 82 has a dependent plug 90 for sealingly fitting within the bore 88 of body 80 to seal the bore 88 such that liquid fixing solution 30 cannot exit therefrom from the bottle 28. A downwardly dependent annular lip 92 of cap 82 snap-fits about a radially extending lip 94 of body 80 to positively retain cap 82 in sealing engagement to body 80. A tab 96 facilitates easy lifting of cap 82 from body 80 to permit removal of the fixing solution 30 from bottle 28 through bore 88. The bottle stopper 78 is used by unsnapping the cap 82 from the body 80 and inserting the needle 70 of the small syringe 58 into sealing engagement within the externally opening portion of the bore 88. The small syringe 58 may then receive the fixing solution 30 by inverting of the bottle 28 and partially withdrawing the plunger 62 from body 60.

Another kit component is a cleaning device comprising a cleaning brush 98 having an elongate handle 100 made of twisted wire with a gripping portion 102 and a cleaning portion 104. A plurality of long bristles 106 and short bristles 108 radially extend from the cleaning portion 104. The brush 98 is sized to clean the interiors of both the large syringe 40 and the small syringe 58 following use.

Another kit component is an applicator device for manually applying the matching color of hair coloring composition 16 and 18 to the hair roots. A first applicator device comprises an applicator brush 110 having an elongate handle 112 which is longitudinally tapered. A wide bristle receiving end 114 has a plurality of bristles 116 longitudinally extending therefrom, and an opposite pointed end 118 is for manipulating the user's hair. Respective ends 119 of the bristles 116 are aligned in an orientation perpendicular to the handle 112. The ends 119 of bristles 116 are dipped into the matching color of the hair coloring composition contained in the mixing bowl 36 and is applied to the hair roots using a brushing action.

Another kit component is a plurality of pairs of protective gloves 120 made of a material which is impervious to the hair coloring materials 12 for protecting the user's hands from being colored along with the hair roots. The gloves 120 are made of fused sheets of thin plastic as so as to be disposable. Such gloves 120 are commercially available not pre-packaged individually or in pairs. The gloves 120 are pre-packaged individually or in pairs in tearable packages 121 made of tearable paper, plastic, or foil as known in industry for packaging of items such as moist towlettes and the like. The packages 121 maintain the gloves 120 in a compact folded condition prior to use.

A carrying device for receiving the kit components for storage and transport thereof comprises a drawstring bag 122. The drawstring bag 122 includes a flexible pouch 124 made of cloth or plastic. The pouch 124 has an open mouth 126 surrounded by a sewn-in drawstring 128 to allow opening and closing of the mouth 126. The bag 122 is for storing the kit components including the mixing bowl 36, the stirring stick 37, the large syringe 40, the small syringe 58, the bottle stopper 78, the cleaning brush 98, the applicator brush 110, and the gloves 120 in packages 121 during periods of non-use. The drawstring bag 122 may be of sufficient size to also hold the hair coloring materials 12.

The coloring kit 10 is used with the coloring materials 12 to color the uncolored outgrown roots of the user's hair to match the previously colored hair shafts as follows. The kit components are removed from the drawstring bag 122 by first loosening the drawstring 128. A pair of the protective gloves 120 is removed from the package 121 by tearing and are donned by the user to protect the user's hands (not shown). The screw cap 22 is then removed from one tube 20. The needle 50 of the large syringe 40 is inserted into the neck 24 of one of the tubes 20 which is squeezed using one of the user's hands. The plunger 42 is simultaneously partially withdrawn from the body 41 by pressing two fingers of the user's other hand against the finger engaging tabs 48 with the thumb of the same hand inserted through the thumb ring 54. When the bottom of the piston 56 reaches the desired position on measuring indicia 46 indicating the necessary quantity of hair coloring composition 16 or 18 is within the large syringe 40, withdrawal of plunger 42 is stopped. The needle 50 is then removed from the neck 24 and placed over the bowl 36. The plunger 42 then depressed back into the body 41 such that the hair coloring composition 16 or 18 is ejected from needle 50 and deposited into mixing bowl 36. The process is repeated with the other tubes 20 to deposit the necessary quantities of the other of hair coloring compositions 16 and 18 into the mixing bowl 36.

The necessary quantities of the hair coloring compositions 16 and 18 (and others if used) are manually mixed together within the mixing bowl 36 using the spatula 39 of the stirring stick 37 using circular and/or back-and-forth motions. The necessary quantities of the hair coloring compositions 16 and 18 are either known from previous experience coloring the user's hair, or an educated guess. If the color of the mixed hair coloring composition in the mixing bowl 36 is not the matching color to the hair roots, additional of the hair coloring compositions 16 and 18 may be measured and added to fine-tune the color.

The screw cap 32 is removed from the bottle 28 and the body 80 of bottle stopper 78 is firmly pressed into neck 34 until the stepped outer surface 86 firmly seats therein. The cap 82 is then unsnapped from body 80 using the tab 96, being retained thereto by the strap 84. The needle 70 of the small syringe 58 is inserted into sealing engagement within the externally opening portion of the bore 88. The small syringe 58 may then receive the fixing solution 30 by inverting of the bottle 28 held in one of the user's hands and simultaneously partially withdrawing the plunger 62 from the body 60 by pressing two fingers of the user's other hand against the finger engaging tabs 68 with the thumb of the same hand engaging the finger disk 74. When the bottom of the piston 76 reaches the desired position on measuring indicia 66 indicating the necessary quantity of fixing solution 30 is within the small syringe 58 for the amount of mixed coloring composition, withdrawal of plunger 62 is stopped. The bottle 28 is then brought back to an upright position and the needle 70 is removed from the bore 88 and placed over the mixing bowl 36. The plunger 62 then depressed back into the body 60 such that the fixing solution 30 is ejected from needle 70 and deposited into mixing bowl 36. The mixed hair coloring composition and the fixing solution 30 are manually mixed together within the mixing container 36 using the spatula 39 of the stirring stick 37 using circular and/or back-and-forth motions.

The matching color of hair coloring composition is applied to the hair roots using the applicator brush 110 by dipping the ends 119 of bristles 116 into the mixed hair coloring composition contained in the mixing bowl 36. The bristles 116 with adhered mixed hair coloring composition are brushed against the hair roots using a brushing action in conventional manner. The hair coloring composition applied to the hair roots is allowed to remain on the hair roots and then washed off according to the instructions for the hair coloring materials 12.

The kit components including mixing bowl 36, stirring stick 37, large syringe 40, small syringe 58, bottle stopper 78, and applicator brush 110, are cleaned using conventional paper towels and solvent such as water. The brush 98 is used to clean hard-to-reach areas such as the bore 88 of bottle stopper 78, the needles 50 and 70 of the syringes 40 and 58, and the like. The gloves 120 may then be removed from the user's hands, turned inside-out to prevent unwanted spreading of the adhering hair coloring composition, and disposed of. The cleaned kit components and the coloring materials 12 are then stored in the drawstring bag 122.

Shown in FIG. 2 is a second embodiment hair roots coloring kit 130 of the present invention shown with the hair coloring materials 12 disposed on the table surface 13. The hair roots coloring kit 130 is used for mixing together any of the variety of types standard commercially available hair coloring materials 12 explained previously.

The coloring kit 130 includes a plurality of kit components such as a mixing container for holding the necessary quantities of the hair coloring materials to produce the matching color of hair coloring composition. A plurality of second mixing bowls 132 are molded from of a thin sheet material such as plastic, paper, or coated paper so as to be disposable which are made to closely nest together. The mixing bowls 132 are used to contain the different colors of hair coloring compositions 16 and 18 during mixing together to form the matching color for the hair and for mixing in the fixing solution 30 to set the matching color prior to applying to the hair roots.

Another kit component is a stirring device comprising a plurality of second stirring sticks 134 for manually mixing together of the necessary quantities of the hair coloring materials 16 and 18 within the mixing bowls 132 to produce the matching color of hair coloring composition. The stirring sticks 134 are disposable, being made of a substantially rigid and disposable material such as coated paper, plastic, or wood. The stirring sticks include an elongate handle 136 of a flat cross-section and a dependent flat spatula 138 for mixing of the hair coloring compositions 16 and 18, and the fixing solution 30 in the mixing bowls 132.

Another kit component is at least one measuring device provided for measuring the necessary quantities of the hair coloring compositions 16 and 18 to produce the matching color of hair coloring composition. This includes the large syringe 40 used for measuring the hair coloring compositions 16 and 18 from the tubes 20 into the bowls 132.

Another kit component is a third measuring device comprising an eyedropper 140 for measuring the fixing solution 30 from the bottle 28. The eyedropper 140 includes an elongate tubular body 142 and a squeezable bulb 144. The body 142 is made of glass or plastic and has a mid-section 146 with a measuring indicia 148, a gripping end 150 over which an open end 152 of bulb 144 is affixed, and a tapered open end 154 to receive the fixing solution 30 through the bottle stopper 78 similarly to the small syringe 58.

Another kit component is a fourth measuring device comprising a measuring cup 156 for receiving and measuring the fixing solution 30 removed from the bottle 28 using the eyedropper 140. The measuring cup 156 includes a circular bottom wall 158, an upstanding annular side wall 160 with a pouring spout 162, and a measuring indicia 164.

Another kit component is the cleaning brush 98 which is of such a size so as to also allow cleaning of the eyedropper 140 following use.

Another kit component is an applicator device for manually applying the matching color of hair coloring composition 16 and 18 to the hair roots. An applicator device comprises a second applicator brush 166 of similar design to brush 110. Applicator brush 166 includes an elongate handle 168 which is longitudinally tapered. A wide bristle receiving end 170 has a plurality of bristles 172 longitudinally extending therefrom, and an opposite curled end 174 for manipulating the user's hair. Respective ends 176 of the bristles 172 are aligned in an orientation angled relative to the handle 168. The ends 176 of bristles 172 are dipped into the matching color of the hair coloring composition contained in the mixing bowls 132 and is applied to the hair roots using a brushing action.

Another kit component is the plurality of disposable gloves 120 in the tearable packages 121 provided for use in protecting the user's hands from being colored along with the hair roots.

The drawstring bag 122 is used for receiving the kit components for storage and transport thereof including the large syringe 40, the cleaning brush 98, the gloves 120 in packages 121, the mixing bowls 132, the stirring sticks 134, the eyedropper 140, the measuring cup 156, and the applicator brush 166 during periods of non-use. The drawstring bag 122 may be of sufficient size to also hold the hair coloring materials 12.

The coloring kit 130 is used with the coloring materials 12 to color the uncolored outgrown roots of the user's hair to match the previously colored hair shafts as follows. The coloring kit components 130 are removed from the drawstring bag 122 by first loosening the drawstring 128. A pair of the protective gloves 120 is removed from the package 121 by tearing and donned by the user to protect the user's hands. The screw cap 22 is then removed from one tube 20. The needle 50 of the large syringe 40 is inserted into the neck 24 of one of the tubes 20 which is squeezed using one of the user's hands. The plunger 42 is simultaneously partially withdrawn from the body 41 by pressing two fingers of the user's other hand against the finger engaging tabs 48 with the thumb of the same hand inserted through the thumb ring 54. When the bottom of the piston 56 reaches the desired position on measuring indicia 46 indicating the necessary quantity of hair coloring composition 16 or 18 is within the large syringe 40, withdrawal of plunger 42 is stopped. The needle 50 is then removed from the neck 24 and placed over one of the bowls 132. The plunger 42 then depressed back into the body 41 such that the hair coloring composition 16 or 18 is ejected from needle 50 and deposited into mixing bowl 132. The process is repeated with the other tubes 20 to deposit the necessary quantities of the other of hair coloring compositions 16 and 18 into the mixing bowl 132.

The necessary quantities of the hair coloring compositions 16 and 18 (and others if used) are manually mixed together within the mixing bowl 132 using the spatula 138 of the stirring stick 134 using circular and/or back-and-forth motions. The necessary quantities of the hair coloring compositions 16 and 18 are either known from previous experience coloring the user's hair roots, or an educated guess. If the color of the mixed hair coloring composition in the mixing bowl 132 is not the matching color to the hair roots, additional of the hair coloring compositions 16 and 18 may be measured and added to fine-tune the color.

The screw cap 32 is removed from the bottle 28 by inserting the open end 154 of the eyedropper 140 through the neck 34 of bottle 28 into the fixing solution 30 by squeezing and releasing the bulb 144 several times using two fingers of the user's other hand. When the eyedropper 140 is full of fixing solution 30, the open end 154 of the eyedropper 140 is removed from the bottle 28 and placed over the measuring cup 156. The bulb 144 is then depressed and released as needed such that the fixing solution 30 is ejected from open end 154 and deposited into measuring cup 156 to a desired level on the measuring indicia 164. The measured fixing solution 30 is then poured from the measuring cup 156 into the mixing bowl 132. The mixed coloring composition and the fixing solution 30 are manually mixed together within the mixing bowl 132 using the spatula 138 of the stirring stick 134 using circular and/or back-and-forth motions.

The matching color of hair coloring composition is applied to the hair roots using the applicator brush 166 by dipping the ends 176 of bristles 172 into the mixed hair coloring composition contained in the mixing bowl 132. The bristles 172 with adhered hair coloring composition are brushed against the hair roots using a brushing action in conventional manner. The hair coloring composition applied to the hair roots is allowed to remain on the hair roots and then washed off according to the instructions for the hair coloring materials 12.

The kit components including large syringe 40, mixing bowls 132, stirring sticks 134, measuring cup 156, and applicator brush 166 are cleaned using conventional paper towels and solvent such as water. The brush 98 is used to clean hard-to-reach areas such as the needle 50 of the large syringe 40, the interior of the eyedropper 140, and the like. The gloves 120 may then be removed from the user's hands, turned inside-out to prevent unwanted spreading of the adhering hair coloring composition, and disposed of. The cleaned kit components and the coloring materials 12 are then stored in the drawstring bag 122.

The method for coloring the uncolored outgrown roots of a user's hair to match the previously colored hair shafts comprises the steps of: 1) providing a plurality of containers of hair coloring materials including different colored hair coloring compositions; 2) providing a carrying device and a plurality of coloring kit components including at least one measuring device, a mixing container, a stirring device, and an applicator device contained therein; 3) removing the coloring kit components from the carrying device; 4) opening the containers of hair coloring materials; 5) measuring necessary quantities of the hair coloring materials removed from the containers using measuring device to form a matching color of hair coloring composition to the user's hair and depositing into the mixing container; 6) manually mixing together the necessary quantities of the hair coloring materials within the mixing container using the stirring device to form the matching color of hair coloring composition; 7) manually applying the matching color of hair coloring composition from the mixing container onto the roots of the user's hair using the applicator device; 8) preparing the coloring kit components for storage; and 9) replacing the coloring kit components into the carrying device.

The step of providing a plurality of containers of hair coloring materials may include providing a hair coloring composition in the form of a hair coloring paste packaged in a squeezable tube having an outlet neck. The step of providing a carrying device and a plurality of coloring kit components may include providing a measuring device comprising a syringe having an elongate tapered needle adapted to be closely received within the neck of the squeezable tube. The step of measuring necessary quantities of the hair coloring materials may include inserting the tapered needle within the neck and squeezing the tube to receive the hair coloring composition therefrom.

The method may be conducted wherein the plurality of coloring kit components provided are of a cleanable reusable type. The step of preparing the coloring kit components for storage may comprise cleaning the coloring kit components. The step of providing a carrying device and a plurality of coloring kit components may include providing a plurality of disposable mixing containers and stirring devices. The step of preparing the coloring kit components for storage may comprise disposing of used mixing containers and stirring sticks, and cleaning the other coloring kit components used.

The step of providing a carrying device and a plurality of coloring kit components may include providing a pair of protective gloves and a cleaning brush. At least some of the plurality of coloring kit components provided may be of a cleanable reusable type. The step of preparing the coloring kit components for storage may comprise cleaning at least some of the coloring kit components using the which are of the cleanable reusable type using the cleaning brush. Further steps may be added such as putting on the protective gloves prior to measuring necessary quantities of the hair coloring materials and removing the protective gloves after applying the matching color of hair coloring composition to the roots of the user's hair.

Many variations to the present invention are possible while staying within the same inventive concept. Other container devices, measuring devices, stirring devices, applicator devices, and other kit components may be utilized to suit the particular hair coloring materials, compositions, and containers. For example, other applicator brushes may be used as are know in the art including brushes with various handle designs, bristle configurations, and the like. The drawstring bag may be partially or completely made of thin flexible opaque or transparent plastic material. The transparent plastic material allows the kit components to be visible through the drawstring bag. The drawstring bag may be replaced such as by a carrying case made of rigid plastic.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A hair roots coloring kit for mixing together standard hair coloring materials including containers of a plurality of different colored hair coloring compositions to form a matching color of hair coloring composition to a user's previously colored hair shafts and for applying to uncolored outgrown roots of the hair, comprising:
    at least one measuring device adapted for measuring necessary quantities of the hair coloring materials to produce the matching color of hair coloring composition comprising a syringe having a hollow body adapted to closely receive a slidable plunger having a resilient sealing piston, said body having a transparent tubular midsection with a measuring indicia and an elongate tapered needle adapted to be closely received within necks of squeezable tubes to receive the hair coloring composition contained therein in the form of a paste therefrom upon squeezing of the tube, said body having a pair of finger engaging tabs and the piston having a thumb ring to facilitate withdrawal of said piston from said body as the hair coloring paste is squeezed from the tube into said syringe;
    a mixing container adapted for holding the necessary quantities of the hair coloring materials;
    a stirring device adapted for manual mixing together of the necessary quantities of the hair coloring materials within said container to produce the matching color of hair coloring composition;
    an applicator device adapted for manually applying the matching color of hair coloring composition to the roots of the user's hair; and
    a carrying device adapted for receiving said syringe, said stirring device, and said applicator device for storage and transport thereof.

2. The kit according to claim 1, wherein the mixing container comprises a mixing bowl of a type chosen from the group consisting of reusable and disposable.

3. The kit according to claim 2, wherein the mixing bowl is of the reusable type being made of a substantially rigid and cleanable material chosen from the group consisting of glass, ceramic, and plastic.

4. The kit according to claim 2, wherein there are a plurality of mixing bowls which are disposable, being molded from a thin sheet material chosen from the group consisting of plastic, paper, and coated paper which are made to closely nest together.

5. The kit according to claim 2, wherein there are a plurality of the mixing bowls which are disposable, being molded from a thin sheet material chosen from the group consisting of plastic, paper, and coated paper which are made to closely nest together.

6. The kit according to claim 1, wherein the applicator device comprises an applicator brush having an elongate handle from which a plurality of bristles extend.

7. The kit according to claim 6, wherein the handle of the applicator brush is longitudinally tapered, having a wide bristle receiving end from which the plurality of bristles longitudinally extend, and an opposite end adapted for manipulating hair of a type chosen from the group consisting of a pointed end and a curled end.

8. The kit according to claim 7, wherein respective ends of the bristles are aligned relative to the handle in an orientation chosen from the group consisting of perpendicularly and angled.

9. The kit according to claim 1, wherein the stirring device comprises a stirring stick of a type chosen from the group consisting of reusable and disposable.

10. The kit according to claim 9, wherein the stirring stick is of the reusable type being made of a substantially rigid and cleanable material chosen from the group consisting of glass, plastic, and wood.

11. The kit according to claim 9, wherein there are a plurality of stirring sticks which are disposable, being made of a material chosen from the group consisting of coated paper, plastic, and wood.

12. The kit according to claim 1, wherein the carrying device comprises a drawstring bag.

13. The kit according to claim 12, wherein the drawstring bag is of a sufficient size to also hold the hair coloring materials.

14. The kit according to claim 1, further comprising an additional kit component chosen from the group consisting of a pair of protective gloves and a cleaning brush.

15. The kit according to claim 14, wherein the additional kit component comprises a plurality of pairs of the protective gloves which are made of fused sheets of thin plastic so as to be disposable.

16. The kit according to claim 15, wherein the gloves are pre-packaged in tearable packages to maintain said gloves in a compact folded condition prior to use.

17. The kit according to claim 14, wherein the additional kit component comprises the cleaning brush having an elongate handle with a gripping portion and a cleaning portion to which a plurality of bristles radially extend.

18. A hair roots coloring kit for mixing together standard hair coloring materials including containers of a plurality of different colored hair coloring compositions to form a matching color of hair coloring composition to a user's previously colored hair shafts and for applying to uncolored outgrown roots of the hair, comprising:
    at least one measuring device adapted for measuring necessary quantities of the hair coloring materials to produce the matching color of hair coloring composition comprising a syringe having a hollow body adapted to closely receive a slidable plunger having a resilient sealing piston, said body having a transparent tubular midsection with a measuring indicia and an elongate tapered needle adapted to be closely received within necks of squeezable tubes to receive the hair coloring composition contained therein in the form of a paste therefrom upon squeezing of the tube;
    a mixing container adapted for holding the necessary quantities of the hair coloring materials;
    a stirring device adapted for manual mixing together of the necessary quantities of the hair coloring materials within said container to produce the matching color of hair coloring composition;
    an applicator device adapted for manually applying the matching color of hair coloring composition to the roots of the user's hair; and
    a bottle stopper which includes a longitudinally tapered, resilient body of circular cross-section and a recloseable cap, said body being adapted to closely fit within the necks of variously sized bottles and having a longitudinal bore which extends through said body, an externally opening portion of said bore being of such a size to closely receive the tapered needle of the syringe to receive the hair coloring composition contained therein in the form of a liquid upon inverting of the bottle, said cap being adapted to sealingly attach to said body to prevent the liquid from exiting the bottle through said bore; and a carrying device adapted for receiving said measuring device, said stirring device, and said applicator device for storage and transport thereof.

19. The kit according to claim 18, wherein the cap is disk-shaped and attached to the body by a connecting strap, the outer surface of the body is annularly stepped, and the cap has a dependent plug adapted to sealingly fit within the bore of said body to seal said bore such that liquid cannot exit therefrom.

20. A hair roots coloring kit for mixing together standard hair coloring materials including containers of a plurality of different colored hair coloring compositions to form a matching color of hair coloring composition to a user's previously colored hair shafts and for applying to uncolored outgrown roots of the hair, comprising:

at least one measuring device adapted for measuring desired quantities of the hair coloring compositions chosen from the group consisting a measuring cup, a syringe, and an eyedropper;

a mixing container adapted for holding the desired quantities of the hair coloring materials comprising a mixing bowl of a type chosen from the group consisting of reusable and disposable;

a stirring device adapted for manual mixing together of the desired quantities of the hair coloring materials within said container to produce the desired color hair of coloring composition;

an applicator device adapted for manually applying the desired color of hair coloring composition to the roots of the user's hair;

a bottle stopper which includes a longitudinally tapered, resilient body of circular cross-section and a recloseable cap, said body being adapted to closely fit within the necks of variously sized bottles and having a longitudinal bore which extends through said body, an externally opening portion of said bore being of such a size to closely receive the tapered needle of the syringe to receive the hair coloring composition contained therein in the form of a liquid upon inverting of the bottle, said cap being adapted to sealingly attach to said body to prevent the liquid from exiting the bottle through said bore; and a carrying device adapted for receiving said measuring device, said stirring device, and said applicator device for storage and transport thereof.

21. The kit according to claim 20, wherein the measuring device comprises a syringe having a hollow body adapted to closely receive a slidable plunger having a resilient sealing piston, said body having a transparent tubular mid-section with a measuring indicia and an elongate tapered needle adapted to be closely received within necks of squeezable tubes to receive the hair coloring composition contained therein in the form of a paste therefrom upon squeezing of the tube.

22. The kit according to claim 21, wherein the body of the syringe includes a pair of finger engaging tabs and the plunger includes a thumb ring to facilitate withdrawal of said plunger from said body as the hair coloring paste is squeezed from the tube into said syringe.

23. The kit according to claim 20, further comprising:

an additional kit component chosen from the group consisting of a pair of protective gloves and a cleaning brush; and wherein the applicator device comprises an applicator brush having an elongate handle from which a plurality of bristles extend, the carrying device comprises a drawstring bag, and the stirring device comprises a stirring stick of a type chosen from the group consisting of reusable and disposable.

24. The kit according to claim 20, wherein the measuring device comprises a measuring cup having a circular bottom wall, an upstanding annular side wall with a measuring indicia, and a pouring spout.

25. The kit according to claim 20, wherein the measuring device comprises an eyedropper having an elongate tubular body and a squeezable bulb.

* * * * *